US010028320B2

(12) United States Patent
Poulo

(10) Patent No.: US 10,028,320 B2
(45) Date of Patent: Jul. 17, 2018

(54) CONTACTLESS INFORMATION TRANSFER IN CT IMAGING MODALITY

(71) Applicant: ANALOGIC CORPORATION, Peabody, MA (US)

(72) Inventor: Louis R. Poulo, Andover, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 393 days.

(21) Appl. No.: 14/440,417

(22) PCT Filed: Nov. 2, 2012

(86) PCT No.: PCT/US2012/063152
§ 371 (c)(1),
(2) Date: May 4, 2015

(87) PCT Pub. No.: WO2014/070190
PCT Pub. Date: May 8, 2014

(65) Prior Publication Data
US 2015/0289306 A1 Oct. 8, 2015

(51) Int. Cl.
*A61B 6/00* (2006.01)
*H04W 76/14* (2018.01)
*H04L 27/26* (2006.01)
*H04L 12/24* (2006.01)
*H04W 76/02* (2009.01)

(52) U.S. Cl.
CPC .............. *H04W 76/14* (2018.02); *A61B 6/56* (2013.01); *H04L 27/26* (2013.01); *H04L 41/0803* (2013.01); *H04W 76/023* (2013.01)

(58) Field of Classification Search
CPC ....... A61B 6/032; A61B 6/56; H04W 76/023; H04W 76/14; H04L 27/26; H04L 41/0803
See application file for complete search history.

(56) References Cited

U.S. PATENT DOCUMENTS

| 4,378,472 A | 3/1983 | Lechner |
| 5,577,026 A * | 11/1996 | Gordon .................... H01Q 1/38 343/841 |
| 2006/0274853 A1 | 12/2006 | Schilling |
| 2007/0035883 A1* | 2/2007 | Katcha ..................... A61B 6/56 360/281.8 |
| 2009/0304144 A1 | 12/2009 | Beyerlein et al. |

OTHER PUBLICATIONS

International Search Report cited in related application No. PCT/US12/63152 dated Jul. 22, 2013, pp. 12.

* cited by examiner

*Primary Examiner* — Courtney Thomas
(74) *Attorney, Agent, or Firm* — Cooper Legal Group, LLC

(57) ABSTRACT

Among other things, a communication system and technique for transferring information between a stationary unit and a rotating unit of a computed tomography (CT) system is provided. The communication system comprises a transceiver and a contactless data-link comprising at least one physical channel. The transceiver is configured to create at least two logical channels from a single physical channel to provide for transmitting at least two types of information in a single direction and/or to provide for transmitting information bi-directionally. In this manner, an amount of data that can be transmitted over a single physical channel can be increased.

20 Claims, 7 Drawing Sheets

CONTACTLESS INFORMATION TRANSFER IN CT IMAGING MODALITY

BACKGROUND

The present application relates to the transference of information across an airgap. It finds particular application in the context of computed tomography (CT) imaging modalities, which may be utilized in medical, security, and/or industrial applications, for example, where data is transferred between a rotating member and a stationary member via a contactless transfer system. It may also apply to other applications where data, such as imaging data and/or control data, for example, is wirelessly transferred between a transmitter and a receiver.

Today, CT imaging modalities (e.g., including single-photon emission computed tomography (SPECT) systems) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

CT systems are typically configured to generate volumetric data corresponding to an object under examination. To generate this volumetric data, the CT system is generally configured to rotate a radiation source and detector array about the object under examination (e.g., causing the object to be viewed from a plurality of angles). For example, the radiation source and/or detector array may be mounted to a rotating member (at times referred to as a rotor or rotating gantry) configured for rotation relative to a stationary member (at times referred to as a stator) configured to support the rotating member.

Given that the radiation source and detector array are mounted on the rotating member, power, control information (e.g., instructing the radiation source and/or other electronic components how to operate), and/or timing signals are typically supplied to the rotating member from the stationary member. Moreover, imaging data (e.g., data generated in response to the detection of radiation by the detector array) and/or control information (e.g., regarding controls or statuses of the radiation source and/or other components attached to the rotating member) are typically transferred from the rotating member to the stationary member (e.g., for further processing and/or to be displayed to security/medical personnel). It may be appreciated that the volume of data transferred, particularly with respect imaging data, may be quite large. For example, some imaging modalities may require transfer speeds of up to 1.5 or more gigabits per second (e.g., particularly if the rotating member does not comprise a storage medium to temporarily store imaging data until it can be transferred).

Conventionally, slip-ring assemblies have been used to transfer power and/or information (e.g., control information, timing information, and/or imaging data) between the stationary member and the rotating member or more generally between a movable member and a stationary member (or between two movable members) through the physical contact of two materials (e.g., via a sliding contact). For example, a slip-ring attached to the stationary member may comprise metal brushes that are configured to physically contact electrically conductive surfaces (e.g., metal brushes) comprised on a slip-ring attached to the movable member, allowing power and/or information to be transferred between the stationary member and the movable member through one or more metal brushes.

While the use of slip-ring assemblies has proven effective for transferring power and/or information between a stationary unit and a movable unit (e.g., such as a rotating member) and/or between two movable members, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may, among other things, cause interference during CT imaging. Other drawbacks of slip-ring assemblies may include cost and complexity of manufacture due to special materials and/or mechanical precision that may be required.

More recently, contactless assemblies have been devised to transfer the data between a rotating member and a stationary member. For example, U.S. Pat. No. 5,577,026, assigned to Analogic Corporation and incorporated herein by reference, describes an approach for contactless assemblies configured to transfer data between a rotating member and a stationary member.

SUMMARY

Aspects of the present application address the above matters, and others. According to one aspect, a communication system for communicating information between a rotating member and a stationary member of a computed tomography (CT) system is provided. The system comprises a contactless data-link comprising a rotating portion operably coupled to the rotating member of the CT system and a stationary portion operably coupled to the stationary member of the CT system. The rotating portion is separated from the stationary portion via an airgap, and the contactless data-link comprises at least one physical channel. The system also comprises a transceiver configured to create at least two logical channels over the contactless data-link via the physical channel.

According to another aspect, a method for communicating information between a rotating member and a stationary member of a computed tomography (CT) system is provided. The method comprises creating at least two logical channels over a contactless data-link that communicatively couple the rotating member and the stationary member. A first logical channel of the at least two logical channels is configured to communicate a first type of information in a first direction. A second logical channel of the at least two logical channels configured to at least one of communicate the first type of information in a second direction; communicate a second type of information in the second direction; or communicate the second type of information in the first direction.

According to another embodiment, a computed tomography (CT) system is provided. The system comprises a radiation source, a detector array, and a rotating member configured to rotate the radiation source and the detector array about an object under examination. The system also comprises a contactless data-link comprising a rotating portion operably coupled to the rotating member and a stationary portion operably coupled to a stationary member of the CT system. The rotating portion is separated from the stationary portion via an airgap. The system further comprises a transceiver configured to provide for two-way communication via a physical channel of the contactless data-link.

Those of ordinary skill in the art may appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
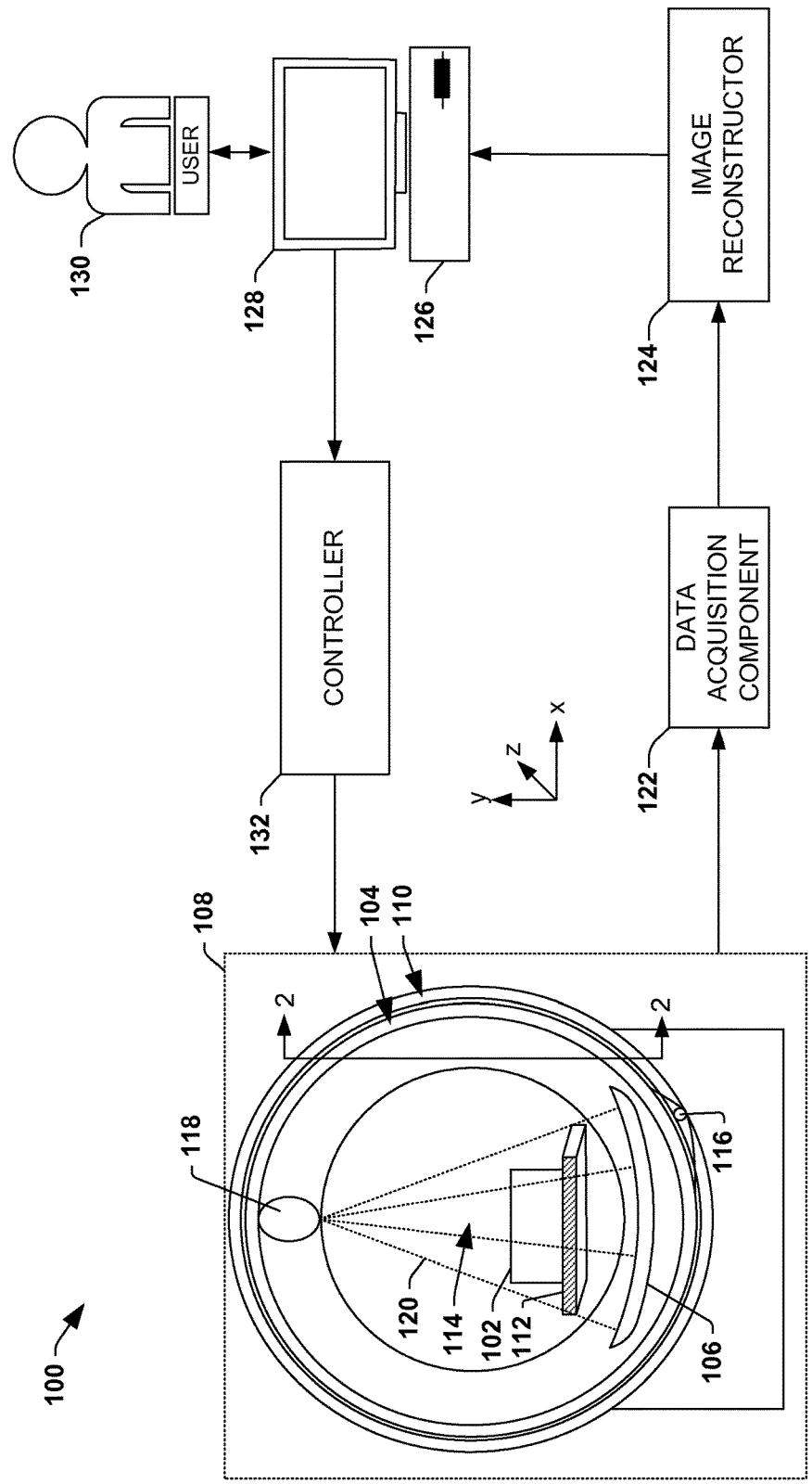
FIG. 1 is a schematic block diagram illustrating an example environment where a communication system such as described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a communication system for transferring information between two (or more) members. Typically, at least one of the members is movable (e.g., rotatable) relative to the other member and the two members are separated by an airgap. The communication system is at least comprised of a contactless data-link (e.g., comprising at least two antennas or other mediums for the transmission of information) and a transceiver configured to send and/or receive information signals indicative of information to be transferred between the first member and the second member via the contactless data-link.

In one embodiment, the transceiver may be configured to create at least two logical channels for the transmission of information over a physical channel of the contactless data-link. A first logical channel may be utilized for transmitting a first type of information in a first direction and a second logical channel may be utilized for transmitting the first type of information in second direction and/or for transmitting a second type of information in the second direction and/or in the first direction. In this way, one or more types of information may be transmitted bi-directionally over the contactless data-link and/or two or more different types of information may be transmitted over the contactless data-link in a same and/or different direction. Types of information transmitted over the contactless data-link may include, among other things, imaging data, control data, and/or timing information. In some embodiments, the contactless data-link may be configured to support the transfer of information in merely an analog domain or in merely a digital domain, and the transceiver may be further configured to convert information between the analog and digital domains to facilitate transmission over the contactless data-link, for example.

To create the at least two logical channels for transmission of information over a physical channel, the transceiver may comprise a multiplexer and/or a demultiplexer. Such a multiplexer/demultiplexer may utilize multiplexing techniques, such as frequency-division multiplexing, time-division multiplexing, and/or code-division multiplexing, for example, to create the at least two logical channels.

It may be appreciated that "noncontact," "contactless," and/or the like is used herein to refer to the ability to transfer information between or among bodies configured for relative movement, and should not be understood to necessarily preclude possible contact between or among such bodies for other purposes, including, for example, electrostatic discharge, exchange or transmission of data, mechanical drive or support, braking and safety mechanisms, low-voltage power transfer, high-voltage power transfer, etc. It may also be appreciated that in the present disclosure, except where otherwise clear from context, "gap" and "airgap" and/or the like are used more or less interchangeably, and are not intended to be limited to air, it being possible for vacuum, oil, and/or other fluid and/or gas, and/or sliding and/or roller bearings and/or other such contrivances permitting relative movement to completely or partially fill such gaps or spaces.

FIG. 1 is an illustration of an example environment 100 where a communication system as provided for herein, including a transceiver and a contactless data-link (e.g., configured to transfer information across an airgap) may be useful. More particularly, FIG. 1 illustrates an example computed tomography (CT) imaging modality that can be configured to acquire volumetric information regarding an object 102 under examination and generate images therefrom. It may be appreciated that the environment 100 is merely an example and is not intended to be interpreted in a limiting manner, such as necessarily specifying the location, inclusion, and/or relative arrangement of the components depicted therein. For example, a data acquisition component 122 as illustrated in FIG. 1 may be part of a rotating member 104 of an object examination apparatus 108, or more particularly may be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotating member 104 and a stationary member 110. During an examination of the object(s) 102, the object(s) 102 can be placed on a support article 112, such as a bed or conveyor belt, that is selectively positioned in an examination region 114 (e.g., a hollow bore in the rotating member 104), and the rotating member 104 can be rotated about the object(s) 102 by a rotator 116 (e.g., motor, drive shaft, chain, etc.).

The rotating member 104 may surround a portion of the examination region 114 and may comprise one or more radiation sources 118 (e.g., an x-ray source, gamma-ray source, or other ionizing radiation source) and a detector array 106 that is mounted on a substantially diametrically opposite side of the rotating member 104 relative to the radiation source(s) 118. During an examination of the object(s) 102, the radiation source(s) 118 emits fan, cone, wedge, and/or other shaped radiation 120 configurations into the examination region 114 of the object examination apparatus 108. It may be appreciated that such radiation may be emitted substantially continuously and/or may be emitted intermittently (e.g., a short pulse of radiation is emitted followed by a resting period during which the radiation source(s) 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using a scintillator(s) and photo-detectors and/or other indirect conversion materials) detected radiation into signals that can be transmitted from the detector array 106 to a data acquisition component 122 (e.g., typically positioned on the rotating member 104) configured to convert analog signals output by the detector array 106 into digital signals and/or to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that were emitted while the radiation source 118 was at a particular angular range relative to the object 102. Based upon the compiled signals, the data acquisition component 122 can generate projection data indicative of the compiled signals, for example.

Information may be transmitted between components physically attached to the rotating member 104 (e.g., such as the detector array 106 and/or data acquisition component 122) and components that are not physically attached to the rotating member 104 (e.g., such as an image reconstructor 124) through a contactless data-link. By way of example, the projection space data generated by the data acquisition component 122 may be transmitted via a communication system to an image reconstructor 124 positioned on the stationary side of the imaging modality. As may be described in more detail below, such a communication system may comprise, among other things, a first transceiver (e.g., mounted to the rotating member 104), a contactless data-link (e.g., comprising a first antenna mounted to the rotating member 104 and a second antenna mounted to the stationary member 110), and a second transceiver (e.g., mounted to the stationary member 110). In this way, information may be transferred between the rotating member 104 and the stationary member 110.

It may be appreciated that although reference is made herein to the communication system being comprised of first and second transceivers, respective transceiver may not perform both the functions of a receiver and a transmitter. For example, the first transceiver may function merely as a transmitter configured to transmit information across the contactless data-link and the second transceiver may function merely as a receiver configured to receive information transmitted across the contactless data-link and/or vice-versa. In another embodiment, the first transceiver and/or the second transceiver may behave in the tradition sense where the transceiver(s) is configured for both sending and receiving information. Thus, as provided herein, where a transceiver is illustrated and/or described, the transceiver may merely be a receiver or a transmitter. Similarly, where a transmitter or receiver is illustrated and/or described herein, such a transmitter or receiver may comprise a transceiver configured for both transmission and reception.

The image reconstructor 124 is configured to receive the projection space data that is output by the data acquisition component 122 (e.g., or output from the communication system). The image reconstructor 124 is also configured to generate image space data from the projection space data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

As used herein, data or information representative of an object may be referred to herein as imaging data. That is, imaging data may be used to generically refer to data or information in the projection space domain and/or in the image space domain that is representative of an object presently under examination and/or that previously underwent an examination.

The example environment 100 also includes a terminal 126, or workstation (e.g., a computer), configured to receive the image(s), which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive input from the terminal 126, such as user input for example, and to generate instructions for the object examination apparatus 108 indicative of operations to be performed. For example, the user 130 may desire to reexamine the object(s) 102 at a different energy level, and the controller 132 may issue a command instructing the support article 112 to reverse direction (e.g., bringing the object(s) 102 back into an examination region 114 of the object examination apparatus 102).

Figure 2:
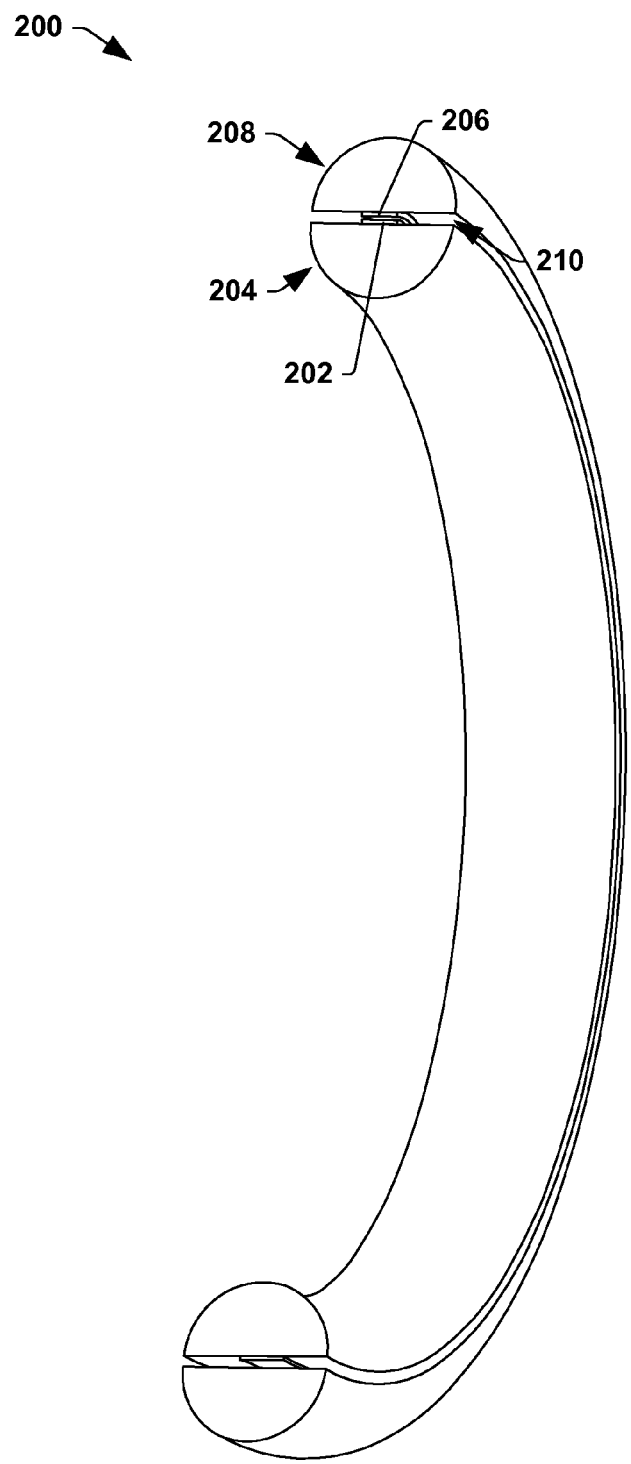
FIG. 2 illustrates an example rotating member and stationary member of a CT system separated by an airgap.

FIG. 2 illustrates a cross-sectional view 200 (e.g., taken along line 2-2 in FIG. 1) of a contactless data-link comprising a first antenna 202 physically coupled to a rotating member 204 (e.g., 104 in FIG. 1) and a second antenna 206 physically coupled to a stationary member 208 (e.g., 110 in FIG. 1).

The rotating member 204 is typically separated from the stationary member 208 by an airgap 210 that is defined by a space between the rotating member 204 and the stationary member 208 and is configured to enable rotation of the rotating member 204 relative to the stationary member 208. Typically the first antenna 202 is mounted on the rotating member 204 within and/or adjacent the airgap 210 and the second antenna 206 is mounted on the stationary member 208 within and/or adjacent the airgap 210, although other arrangements are contemplated. As such, the second antenna 206 may detect electromagnetic waves generated via the first antenna 202 that are propagated through the airgap 210 and/or the first antenna 202 may detect electromagnetic waves generated via the second antenna 206 that are propagated through the airgap.

Respective antennas 202, 206 may be comprised of one or more physical channels respectively configured to convey information between the rotating member 204 and the stationary member 208. Moreover, as may be described in more detail below, a transceiver(s) may be configured create two or more logical channels via a physical channel (e.g., by logically sub-dividing the physical channel into two or more logical channels). In this way, two or more types of information (e.g., respectively represented by different signals) may be transferred in a single direction and/or information may be transferred bi-directionally via a single physical channel, for example. By way of example and not limitation, in one embodiment, the contactless data-link comprises merely (e.g., exactly) one physical channel (e.g., one wire or other physical transmission medium), which a transceiver(s) may utilize to create two or more logical channels.

Although the foregoing cross-sectional view 200 describes a radial airgap 210 (e.g., between the entirety of the outer circumference of the rotating member 204 and entirety of the inner circumference of the stationary member 208), it may be appreciated that the airgap 210, first antenna 202, and/or second antenna 206 may be arranged differently than the example arrangement. For example, in another embodiment, the airgap 210 may be planar (e.g., where the rotating member 204 and the stationary member 208 face one another, as opposed to being concentric), for example, and the transmitting antenna 202 may be mounted on a planar surface of the rotating member 204, for example.

Figure 3:
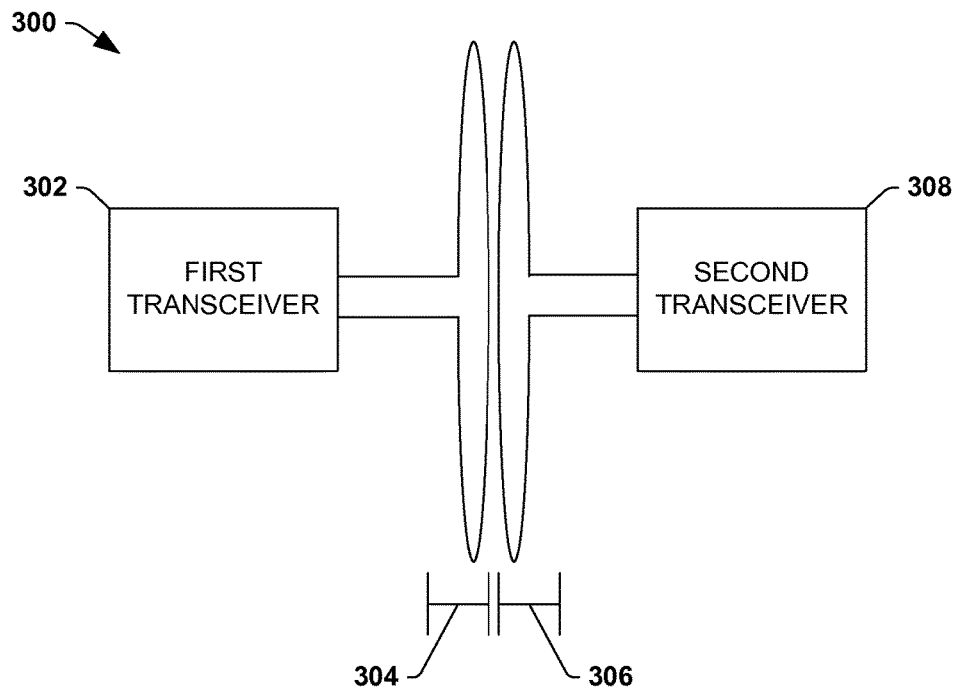
FIG. 3 illustrates a component block diagram of an example communication system.

FIG. 3 illustrates an example communication system 300 configured to communicate information between a rotating member (e.g., 104 in FIG. 1) and a stationary member (e.g., 110 in FIG. 1) via a contactless data-link. By way of example, such a communication system 300 may be configured to communicate imaging data (e.g., indicative of detected radiation) and/or control information (e.g., gate-drive information and/or status information) from the rotating member (e.g., including components attached thereto) to the stationary member (e.g., including components attached thereto) and/or may be configured to communicate control information (e.g., for controlling a radiation source, detector array, and/or other component(s) mounted to the rotating member) and/or timing information from the stationary member to the rotating member. Although such a communication system 300 finds particular application to CT, it may find applicability in other systems where at least one member is movable relative to another member, such as in radar applications, for example.

Coupled to (e.g., or within) the rotating member may be a first transceiver 302 and a rotating portion 304 (e.g., a first antenna 202 in FIG. 2) of the contactless data-link. Coupled to (e.g., or within) the stationary member may be a second transceiver 308 and a stationary portion 306 (e.g., a second antenna 206 in FIG. 2) of the contactless data-link. The first transceiver 302 and/or the second transceiver 308 may be respectively coupled to one or more components configured to provide information (e.g., in the form of digital and/or analog information signals) for conveyance over the contactless data-link. By way of example, the first transceiver 302 may be operably coupled to a data acquisition component (e.g., 122 in FIG. 1) configured to provide a first type of information (e.g., imaging data) to the first transceiver 302 and/or may be operably coupled to a controller of the rotating member configured to provide a second type of information (e.g., control data and/or status information) to the first transceiver 302. The second transceiver 308 may be operably coupled to a controller (e.g., 132 in FIG. 1) configured to provide a third type of information (e.g., control data and/or status information) to the second transceiver 308 and/or a clock configured to provide a fourth type of information (e.g., timing information) to the second transceiver 308. In this way, the first transceiver 302 and/or second transceiver 308 may operate as a transmitter.

Moreover, it may be appreciated that the first transceiver 302 and/or the second transceiver 308 may apply pertinent signal processing techniques to condition and/or prepare a signal for transmission over the contactless data-link. For example, in one embodiment, the contactless data-link may be an analog signal link, and digital data received from one or more components may be converted to an analog domain by the first transceiver 302 and/or the second transceiver 308.

The first transceiver 302 and/or the second transceiver 308 may also operate as a receiver. For example, the second transceiver 308 may be configured to receive information transmitted over the contactless data-link via the first transceiver 302 and/or the first transceiver 302 may be configured to receive information transmitted over the contactless data-link via the second transceiver 308. Moreover, the first transceiver 302 and/or the second transceiver 308 may perform pertinent signal processing techniques on received signals transmitted over the contactless data-link. For example, the first transceiver 302 and/or the second transceiver 308 may be configured to convert a received analog signal to the digital domain and/or to decode information that was encoded by the transceiver transmitting the information over the contactless data-link, for example.

The first transceiver 302 and/or the second transceiver 308 may be further configured to create multiple logical channels through which information may be transferred across the contactless data-link. That is, stated differently, the contactless data link may be comprised of one or more physical channels and the first transceiver 302 and/or the second transceiver 308 may be configured to create two or more logical channels via a physical channel. In this way, a total number of channels available for transferring information across the contactless data-link may be greater than a number of physical channels (e.g., wires or other physical transmission mediums) that comprise the contactless data-link. As an example, a contactless data-link may comprise a single physical channel (e.g., typically permitting the transfer of a single type of information across the contactless data-link in one-direction). By creating two or more logical channels via a physical channel, two or more types of information may be (e.g., concurrently) transferred across the contactless data-link in one direction and/or two or more types of information may be (e.g., concurrently) transferred across the contactless data-link bi-directionally.

By way of example, in one embodiment, two or more logical channels may be created from a single physical channel to facilitate the conveyance of two or more types of information across the data-link (concurrently) in a same direction. For example, the first transceiver 302 may be configured to create two or more logical channels via a single physical channel. A first logical channel of the two or more logical channels may be utilized to transmit a first type of information (e.g., imaging data) across the contactless data-link. A second logical channel of the two or more logical channels may be utilized to transmit a second type of information (e.g., control data, gate-drive information, etc.) across the data-link. In another example, the second transceiver may be configured to create two or more logical channels for transmitting various types of information (e.g., control data, timing information, etc.) across the contactless data-link.

In another embodiment, the creation of two or more logical channels via a physical channel may provide for bi-directional communication across the contactless data-link. For example, a first logical channel of the at least two logical channels may be configured for communication in a first direction (e.g., to support information transmitted across the contactless data-link by the first transceiver 302) and a second logical channel of the at least two logical channels may be configured for communication in a second direction (e.g., to support information transmitted across the contactless data-link by the second transceiver 308). The type of information communicated in the first direction may be a same type of information that is communicated in the second direction or the types of information may be different. In this way, the contactless data-link may support bi-direction communication across a single physical channel, for example.

Respective logical channels may operate substantially independent of other logical channels. Thus, the type of information transmitted across a first logical channel may be different than a type of information transmitted across a second logical channel, a speed or transfer rate of information may differ between logical channels, etc. For example, in one embodiment, a first logical channel may be configured to transmit data at a first bit rate and a second logical channel may be configured to transmit data at a second bit rate that is different than the first bit rate. Moreover, in one embodiment, a transfer rate of one or more logical channels may be adjusted as desired (e.g., so long as the total transfer rate of the logical channels does not exceed a transfer rate of the physical channel comprising the logical channels). For example, during a first portion of an examination of an object, it may be desirable for a first logical channel (e.g., configured to provide control data to the rotating gantry) to have a first transfer rate. Subsequently, once an initial set of instructions has been transmitted to the rotating member via the first logical channel, it may be desired to reduce a transfer rate of the first logical channel and to increase a transfer rate of a second logical channel (e.g., configured to provide status information regarding the rotating member to the stationary member). In this way, the transfer rate of one or more logical channels may be adjusted during an examination and/or during resting periods between examinations, for example, to adjust a flow of information in the communication system 300, for example.

To create the at least two logical channels via the physical channel, a transceiver(s) configured to transmit information (e.g., which may be the first transceiver 302 and/or the second transceiver 308) may comprise a multiplexer and a transceiver(s) configured to receive information transmitted across the data-link (e.g., which may again be the first transceiver 302 and/or the second transceiver 308) may comprise a demultiplexer. The multiplexer is configured to combine multiple information signals (e.g., respectively indicative of a different type of information) into an output signal for transmission across the contactless data-link using one or more multiplexing techniques. For example, the transceiver(s) may be configured to create the at least two logical channels via frequency-division multiplexing, time-division multiplexing, code-division multiplexing, and/or other multiplexing techniques.

The demultiplexer is configured to perform a reverse operation of the multiplexer. That is, the demultiplexer is configured to receive the signal output by the multiplexer (e.g., and transmitted over the contactless data-link) and to separate the output signal into two or more information signals respectively indicative of a type of information that was combined with other types of information to form the output signal. The technique(s) utilized for separating the output signal is typically a function of the multiplexing technique(s) utilized for combining the multiple types of information into one output signal. For example, a plurality of frequency filters may be utilized to separate the output signal based upon frequency where a frequency-division multiplexing technique was utilized to combine the multiple types of information by the multiplexer.

Figure 8:
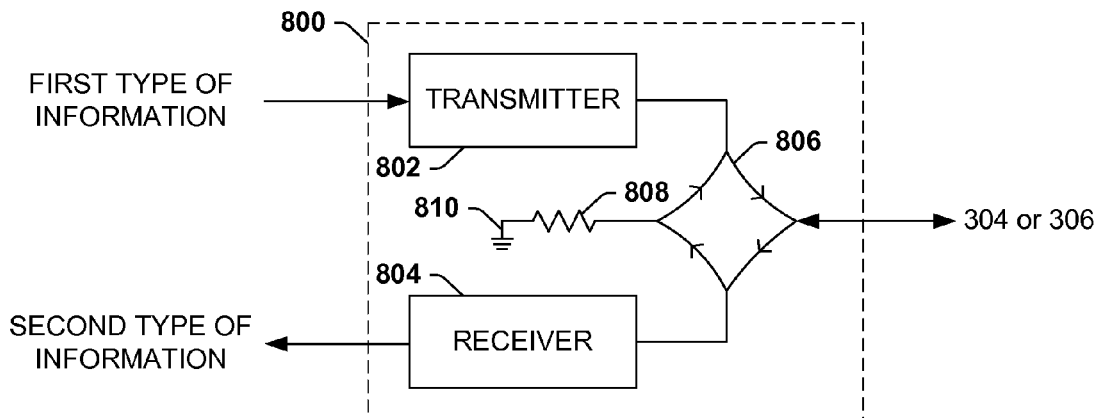
FIG. 8 illustrates a component block diagram of an example transceiver.

In another embodiment, as may be described in FIG. 8, the two or more logical channels may be created via the single physical channel using a circuit hybrid, such as described in U.S. Pat. No. 4,378,472 and incorporated herein by reference. Such a circuit hybrid may be configured to create a first logical channel for transmitting information in a first direction and to create a second logical channel for transmitting information in a second direction by controlling the flow of signal(s). For example, a circuit hybrid may be configured to determine a direction of a signal and to direct signals received from the contactless data-link to a receiver portion of a transceiver and to direct signals transmitted from a transmitter portion of the transceiver to the contactless data-link, for example.

FIGS. 4-9 provide component block diagrams illustrating example components for a transceiver, such as a first transceiver (e.g., 302 in FIG. 3) and/or a second transceiver (e.g., 308 in FIG. 3). It may be appreciated that the components comprised in a transceiver may be a function of, among other things, whether the transceiver is configured to transmit signals via the contactless data-link, to receive signals conveyed across the contactless data-link, or both. Further, the components of a transceiver may be function of a multiplexing technique(s) utilized to create the at least two logical channels, for example. Thus, the illustrated arrangements are merely intended as example arrangements and are not intended to limit the scope of the disclosure, including the scope of the claims. Moreover, components of a first arrangement may be combined with components of a second arrangement to provide additional functionality and/or features. For example, an arrangement configured for frequency-division multiplexing may be combined with an arrangement for time-division multiplexing to create logical channels separated by both time and frequency (e.g., to facilitate the creation of more logical channels than may be possible via frequency-division multiplexing or time-division multiplexing separately).

Figure 4:
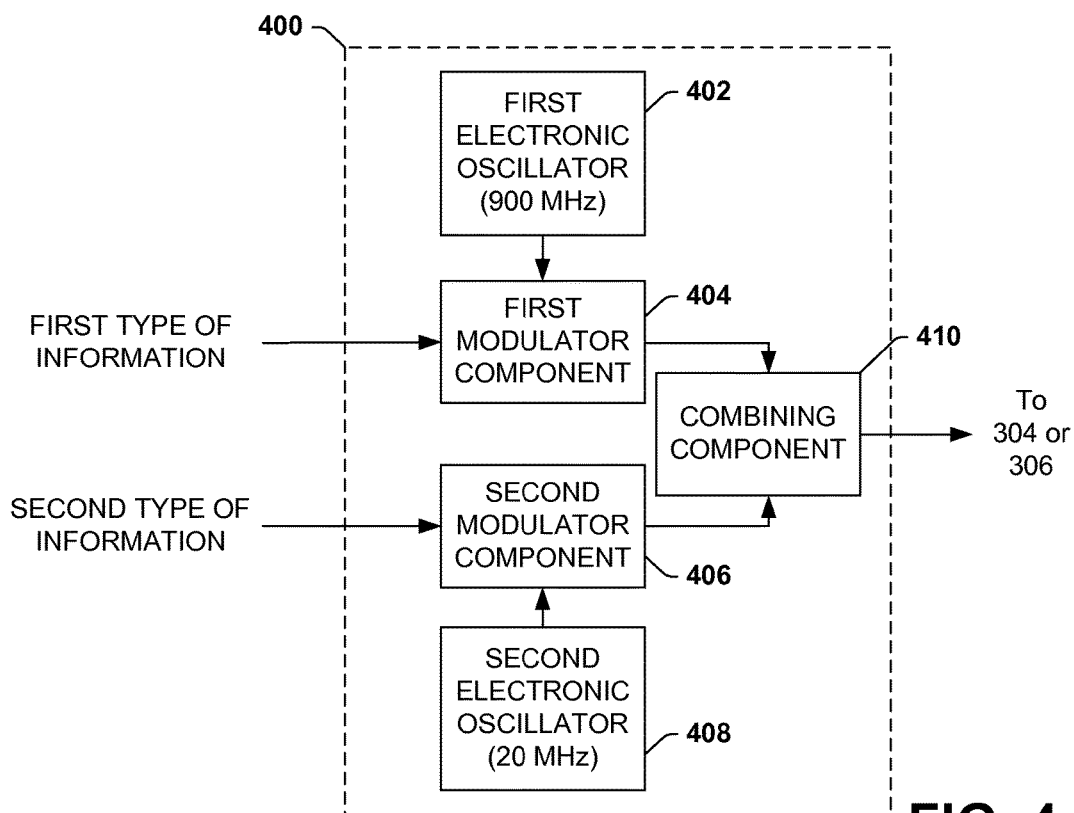
FIG. 4 illustrates a component block diagram of an example transmitter.

With reference to FIG. 4, a transceiver 400 (e.g., 302 and/or 308 in FIG. 3) configured for frequency-division multiplexing is provided. More specifically, FIG. 4 illustrates a transceiver 400 configured to transmit information across the data-link using frequency-division multiplexing. Such a transceiver may be configured to transmit information signals (e.g., indicative of one or more types of information) from a component(s) coupled to a rotating member (e.g., 104 in FIG. 1) or from a component(s) coupled to a stationary member (e.g., 110 in FIG. 1). For example, a data acquisition component (e.g., 122 in FIG. 1) may be configured to provide information signals indicative of a first type of information (e.g., imaging data) to the transceiver 400 and a controller of the rotating member may be configured to provide information signals indicative of a second type of information (e.g., control data) to the transceiver 400. The output of the transceiver may be conveyed to a member of the contactless data-link (e.g., such as a rotating member 304 or a stationary member 306 in FIG. 3) configured to transmit the information across the contactless data-link, for example.

The transceiver 400 may be configured to create a logical channel for respective types of information to be conveyed across the contactless data-link. Thus, in the illustrated embodiment, a first logical channel may be created for transmitting the first type of information and a second logical channel may be created for transmitting the second type of information. It may be appreciated that the first and second logical channels may be part of a same physical channel or the first logical channel may be a part of a first physical channel and the second logical channel may be part of a second physical channel.

For respective logical channels being created, the transceiver 400 may comprise an electronic oscillator and a modulator component. By way of example, in the illustrated embodiment, two types of information are to be transmitted across the contactless data-link by the transceiver 400. As such, the transceiver 400 may create a first logical channel (e.g., configured to facilitate transmission of the first type of information across the contactless data-link) using a first electronic oscillator 402 and a first modulator component 404. The transceiver 400 may create a second logical channel (e.g., configured to facilitate transmission of the second type of information across the contactless data-link) using a second electronic oscillator 408 and a second modulator component 406, for example.

Respective electronic oscillators are configured to generate a carrier signal having a unique frequency (e.g., relative to the frequency of other carrier signals generated by other electronic oscillators). As used herein, a carrier signal may refer to a center frequency of signals within a specified bandwidth or frequency range. For example, in the illustrated embodiment, the first electronic oscillator 402 is configured to generate a carrier signal having a frequency of about 900 MHz (e.g., centered at a first bandwidth ranging from about 850 MHz to about 950 MHz) and the second electronic oscillator is configured to generate a carrier signal having a frequency of about 20 MHz (e.g., centered at a second bandwidth ranging from about 10 MHz to about 30 MHz). It may be appreciated that the frequencies of respective electronic oscillators 402, 408 may depend upon, among other things, a spectrum of frequencies supported by the contactless data-link, a number of logical channels being created, and/or a desired transfer rate of respective logical channels.

Respective modulator components are configured to combine a carrier signal from an electronic oscillator to which the modulator component is operably coupled with an information signal provided by the data acquisition component, controller, etc. For example, in the illustrated embodiment, the first modulator component 404 may be configured to combine a carrier signal output from the first electronic oscillator 402 (e.g., having a frequency of about 900 MHz) with an information signal indicative of the first type of information, and the second modulator component 406 may be configured to combine a carrier signal output from the second electronic oscillator 408 (e.g., having a frequency of about 20 MHz) with an information signal indicative of the second type of information. Accordingly, the first modulator component 404 may be configured to modify one or more properties of a carrier signal output by the first electronic oscillator 402 (e.g., such as amplitude, frequency, or phase) as a function of the information signal indicative of the first type of information and/or the second modulator component 406 may be configured to modify one or more properties of a carrier signal output by the second electronic oscillator 408 as a function of the information signal indicative of the second type of information. In this way, a frequency band occupied by the information signal input into the first modulator component 404 may be different than a frequency band occupied by a signal output by the first modulator component 404 and/or a frequency band occupied by the information signal input into the second modulator component 406 may be different than a frequency band occupied by a signal output by the second modulator component 406, for example. Moreover a bandwidth of the information signal input into the first modulator component 404 may be different than a bandwidth of the signal output by the first modulator component 404 and/or a bandwidth of the information signal input into the second modulator component 406 may be different than a bandwidth of the signal output by the second modulator component 406 (e.g., depending upon a modulation scheme), for example.

In the example transceiver 400, a combining component 410 is configured to combine the signal output by the first modulator component 404 with the signal output by the second modulator component 406 to generate a signal which may be transmitted across the data link. It may be appreciated that, because the signal output by the first modulator component 404 is within a bandwidth that is different than the signal output by the second modulator component 406, at least two logical channels (e.g., respectively distinguishable based upon frequency) may be created to transmit two or more types of information over a (single) physical channel (concurrently). That is, stated differently, by using two or more distinctive frequency bands, the bandwidth of a physical channel of the contactless data-link may be divided to support the conveyance of multiple types of information (e.g., concurrently).

Figure 5:
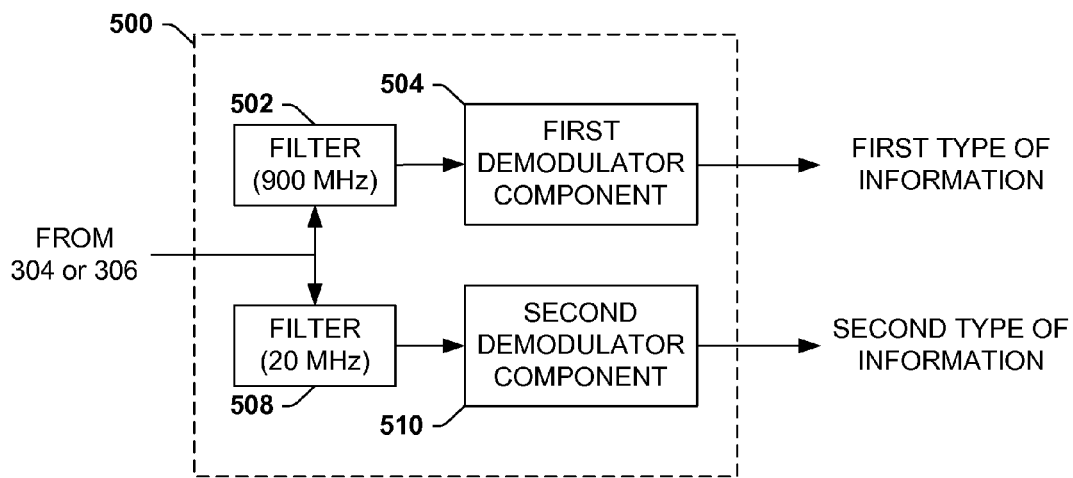
FIG. 5 illustrates a component block diagram of an example receiver.

With reference to FIG. 5, a transceiver 500 (e.g., 302 and/or 308 in FIG. 3) configured for frequency-division multiplexing is provided. More specifically, FIG. 5 illustrates a transceiver 500 configured to receive one or more signals (e.g., from a contactless data-link) multiplexed using a frequency-division multiplexing technique. That is, stated differently, whereas FIG. 4 may illustrate a transmitting portion of a communication system configured for frequency-division multiplexing to create multiple logical channels, FIG. 5 may illustrate a receiving portion of the communication system. The received signal(s) may comprise one or more carrier portions and one or more information portions, for example.

Such a transceiver 500 may be configured to receive information from a contactless data-link (e.g., such as from a rotating member 304 or a stationary member 306 of FIG. 3), separate the received information into component parts and output respective component parts to a designated component(s) of the CT system, for example. By way of example, a signal(s) received by the transceiver 500 may be indicative of a first type of information (e.g., image data) and a second type of information (e.g., control data), and the transceiver 500 may be configured to separate the information by type—transmitting the first type of information to an image reconstructor (e.g., 124 in FIG. 1) and transmitting the second type of information to a terminal to be displayed to a user, for example.

For respective logical channels, the transceiver 500 comprises a filter, a demodulator component, and an electronic oscillator. Thus, for a first logical channel, the transceiver 500 may comprise a first filter 502, and a first demodulator component 504. For a second logical channel, the transceiver 500 may comprise a second filter 508 and a second demodulator 510.

The filters are configured to filter the signal(s), permitting a signal having a frequency range within a specified frequency to pass through while excluding signals having a frequency outside of the specified frequency range. The frequency range of respective filters may be a function of the specified frequencies of the carrier waves (e.g., as described with respect to the transceiver 400 of FIG. 4). By way of example, the first filter 502 of the transceiver 500 may be configured to permit signals within a specified frequency range of about 850 MHz to about 950 MHz to pass through (e.g., to correspond with a 900 MHz carrier signal generated by a first electronic oscillator 402 in FIG. 4). Signals outside of this range may be blocked by the first filter 502. The second filter 508 may be configured to permit signals within a specified frequency range of about 10 MHz to about 30 MHz) to pass through (e.g., to correspond with a 20 MHz carrier signal generated by a second electronic oscillator 408 in FIG. 4) while blocking signals outside this range from passing through the second filter 508. In this way, carrier signals having a frequency of about 900 MHz, which may support a first type of information, may pass through the first filter 502 (e.g., but not the second filter 508). Carrier waves having a frequency of about 20 MHz, which may support a second type of information, may pass through the second filter 508 (e.g., but not the first filter 502), for example.

The signals that are permitted to pass through respective filters 502, 504 comprise information (e.g., of a certain type). Demodulator components are configured to extract the information from the carrier signal. For example, the first demodulator component 504, operably coupled to the first filter 502, may be configured to convert a first carrier signal (e.g., passing through the first filter 502) to a different frequency information signal (e.g., substantially equivalent in frequency to a corresponding information signal input into a modulator component on the transmitting side of the communication system. The second demodulator component 510, operably coupled to the second filter 508, may be configured to convert a second carrier signal (e.g., passing through the second filter 508) to a different frequency information signal (e.g., substantially equivalent in frequency to a corresponding information signal input into a modulator component on the transmitting side of the communication system).

Figure 6:
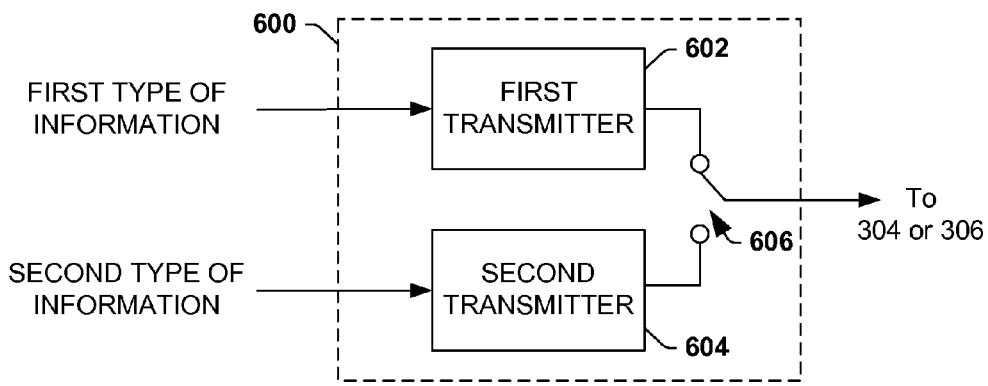
FIG. 6 illustrates a component block diagram of an example transmitter.

With reference to FIG. 6, a transceiver 600 (e.g., 302 and/or 308 in FIG. 3) configured for time-division multiplexing is illustrated. More specifically, FIG. 6 illustrates a transceiver 600 configured to transmit information across the data-link using time-division multiplexing. Such a transceiver 600 may be configured to receive information signals (e.g., indicative of one or more types of information) from a component(s) coupled to a rotating member (e.g., 104 in FIG. 1) or from a component(s) coupled to a stationary member (e.g., 110 in FIG. 1). For example, a data acquisition component (e.g., 122 in FIG. 1) may be configured to provide information signals indicative of a first type of information (e.g., imaging data) to the transceiver 600 and a controller of the rotating member may be configured to provide information signals indicative of a second type of information (e.g., control data and/or status information) to the transceiver 600. The output of the transceiver 600 may be conveyed to a member of the contactless data-link (e.g., such as a rotating member 304 or a stationary member 306 in FIG. 3) configured to transmit the information across the contactless data-link, for example.

The transceiver 600 may be configured to create a logical channel for respective types of information to be conveyed across the contactless data-link. Thus, in the illustrated embodiment, a first logical channel may be created for transmitting the first type of information and a second logical channel may be created for transmitting the second type of information.

To create the logical channels, the transceiver 600 may utilize a time-division multiplexing technique. In such an embodiment, the transceiver 600 divides a time domain into one or more (recurrent) time slots of a fixed length. In one embodiment, the number of time slots is equal to the number of logical channels intended to be created. The time slots may be equal in length or different in length. By way of example, for every 10 milliseconds, the first 8 milliseconds may be assigned to the first logical channel (e.g., through which the first type of information is conveyed) and last 2 milliseconds may be assigned to the second logical channel (e.g., through which the second type of information is conveyed). If the time slots are small (e.g., such that recurrence occurs frequently), it may appear as though two or more types of information are being transferred concurrently (e.g., although the two logical channels may be taking turns on a single physical channel). That is, a first information signal indicative of a first type of information may appear as though it is being conveyed across the contactless data-link simultaneously with a second information signal indicative of the second type of information, although the first information signal and second information signal may flow through a physical channel sequentially.

By way of example, with respect to FIG. 6, the transceiver 600 may be configured to divide the time domain into two time slots to create two logical channels. Moreover, in the illustrated embodiment, respective logical channels (e.g., and time slots) correspond to a different transmitter. For example, a first transmitter 602 of the transceiver 600, configured to transmit a first type of information (e.g., image data) across the contactless data-link, may be configured to convey information during a first 8 milliseconds of a 10 millisecond recurring interval, and a second transmitter 604, configured to transmit a second type of information (e.g., control data) across the contactless data-link, may be configured to convey information during a last 2 milliseconds of the 10 millisecond recurring interval. A switching mechanism 606 may be configured to operably couple the first transmitter 602 to the contactless data-link during the first 8 milliseconds of the 10 millisecond recurring interval and to operably couple the second transmitter 604 to the contactless data-link during the last 2 milliseconds of the 10 millisecond recurring interval, for example. It may be appreciated that the use of a switching mechanism 606 (e.g., which may be optional) may mitigate information signals being transmitted across the data-link unintentionally, for example. Moreover, while FIG. 6 is described with multiple transmitters, respectively configured to transmit a different type of information, in another embodiment, the transceiver 600 may comprise a single transmitter or transceiver configured to convey two or more types of information across the contactless data-link.

It may be appreciated that while reference is made herein to a recurring interval, the time domain may be divided such that one or more time slots are not allocated on a recurring basis. For example, one or more time slots (e.g., in which various types of information are conveyed across the time slot) may be, at times, adjusted to provide for a greater window with which to convey one type of information and/or to reduce a window with which to convey another type of information, for example. Thus, time slots may be not allocated on a static recurring basis, for example. By way of example, the 2 millisecond window associated with the second type of information may not occur for one or more periods to allow for a greater transmission (time) for the first type of information.

Figure 7:
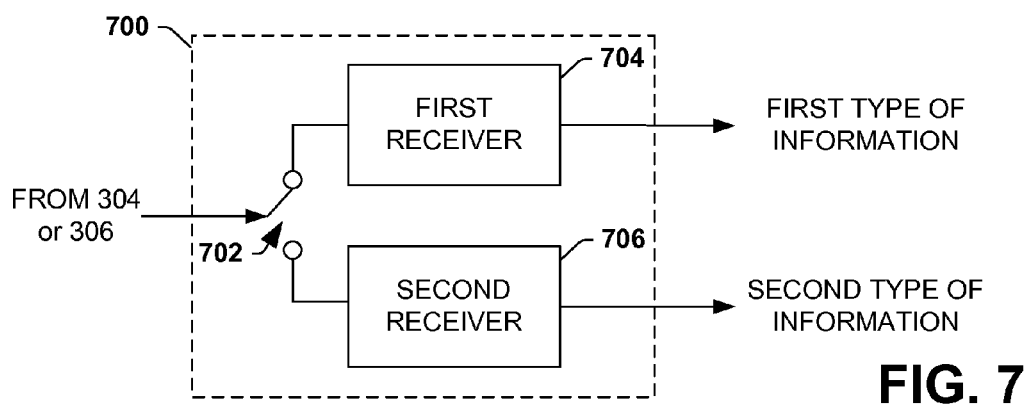
FIG. 7 illustrates a component block diagram of an example receiver.

With reference to FIG. 7, a transceiver 700 (e.g., 302 and/or 308 in FIG. 3) configured for time-division multiplexing is provided. More specifically, FIG. 7 illustrates a transceiver 700 configured to receive one or more signals (e.g., from a contactless data-link) multiplexed using a time-division multiplexing technique. That is, stated differently, whereas FIG. 6 illustrates a transmitting portion of a communication system configured for time-division multiplexing to create multiple logical channels, FIG. 7 illustrates a receiving portion of the communication system.

In the illustrated embodiment, the transceiver 700 comprises a switching mechanism 702 configured to, at times, operably couple a first receiver 704 to a contactless data-link and, at other times, operably couple a second receiver 706 to the contactless data-link. By way of example, the first receiver 704 may be configured to receive information signals from the contactless data-link indicative of the first type of information and the second receiver 706 may be configured to receive information signals from the contactless data-link indicative of the second type of information. Thus, at times when the first type of information is being transmitted (e.g., via a first logical channel), as specified by a multiplexing technique, the switch 702 may be configured to couple the first receiver 704 to the contactless data-link. At other times, when the second type of information is being transmitted (e.g., via a second logical channel), as specified by the multiplexing technique, the switch 702 may be configured to couple the second receiver 706 to the contactless data-link. By way of example, returning to the example provided with respect to FIG. 6, during a first 8 milliseconds of a 10 millisecond interval (e.g., when a first transmitter is configured to transmit information) the switch 702 may be configured to couple the first receiver 704 to the contactless data-link. During a last 2 milliseconds of the 10 millisecond interval (e.g., when a second transmitter is configured to transmit information) the switch 702 may be configured to couple the second receiver 706 to the contactless data-link. In this way, at times when the first transmitter is transmitting information, the switch 702 may route signals to the first receiver 704, and at times when the second transmitter is transmitting information, the switch 702 may route signals to the second receiver 706, for example.

Information signals received by the first receiver 704 and indicative of the first type of information may be decoded, shaped, manipulated, etc. by the first receiver 704 and/or output to a component configured to receive the first type of information. Information signals received by the second receiver 706 and indicative of the second type of information may be decoded, shaped, manipulated, etc. by the second receiver 706 and/or output to a component configured to receive the second type of information.

It may be appreciated that the switching of a switch(s) on a receiving transceiver may be not perfectly in sync with the switching of a switch(s) on a transmitting transceiver. For example, there may be some time delay between when a switch on a transmitting transceiver is switched and when a switch on a receiving transceiver is switched to provide time for signals emitted from a first transceiver to reach a first receiver and/or vice versa. Moreover, it may be appreciated that while the example transceiver 700 comprises a different receiver for respective types of information, in another embodiment, a receiver may be configured to receive multiple types of information. As such, a switch 702 may be optional, for example.

FIG. 8 illustrates yet another embodiment of an example transceiver 800 (e.g., 302 and/or 308 in FIG. 3) configured to create two or more logical channels. Such an example transceiver 800 may find particular applicability to bi-directional communication over a contactless data-link, where a first type of information is transmitted in a first direction and a second type of information is transmitted in a second direction or where the first type of information and/or the second type of information is transmitted in both the first and second direction. By way of example, using such a transceiver 800, stationary components may send control data to rotating components while rotating components may (concurrently) send control data to stationary components. In another embodiment, using such a transceiver 800, stationary components may send control data to the rotating component and rotating components may (concurrently) send imaging data to stationary components, for example.

The example transceiver 800 comprises a transmitter 802, a receiver 804, and a circuit hybrid 806. The transceiver 800 may further comprise a resistor 808 coupled to ground 810, for example. In the illustrated embodiment, the transmitter 802 is configured to receive information signals indicative of a first type of information and to output those signals (e.g., or other signals derived from the received information signals and indicative of the information included in the received signals) to the circuit hybrid 806.

The circuit hybrid 806 is configured to determine a direction of the signal and to direct the signal accordingly. For example, the circuit hybrid 806 may be configured to identify signals output by the transmitter 802 as being intended for the contactless data-link and may route those signals to the contactless data-link. As another example, the circuit hybrid 806 may be configured to identify signals received from the contactless data-link as being intended for the receiver 804 and may be configured to route those signals to the receiver 804. In this way, the circuit hybrid 806 directs the flow of signals as a function of a determined direction of the signal, for example.

A receiver 804 of the transceiver 800 may be configured to receive signals transmitted over the data-link and directed to the receiver 804. Moreover, the receiver 804 may apply pertinent signal processing and/or signal manipulation techniques to output an information signal in a condition desired by a component receiving the signal. In the example embodiment, the receiver 804 is configured to output a second type of information, which is a different type of information than the information type received by the transmitter 802. However, in another embodiment, the receiver 804 may be configured to output a same type of information as the transmitter 802 is configured to receive, for example.

Figure 9:
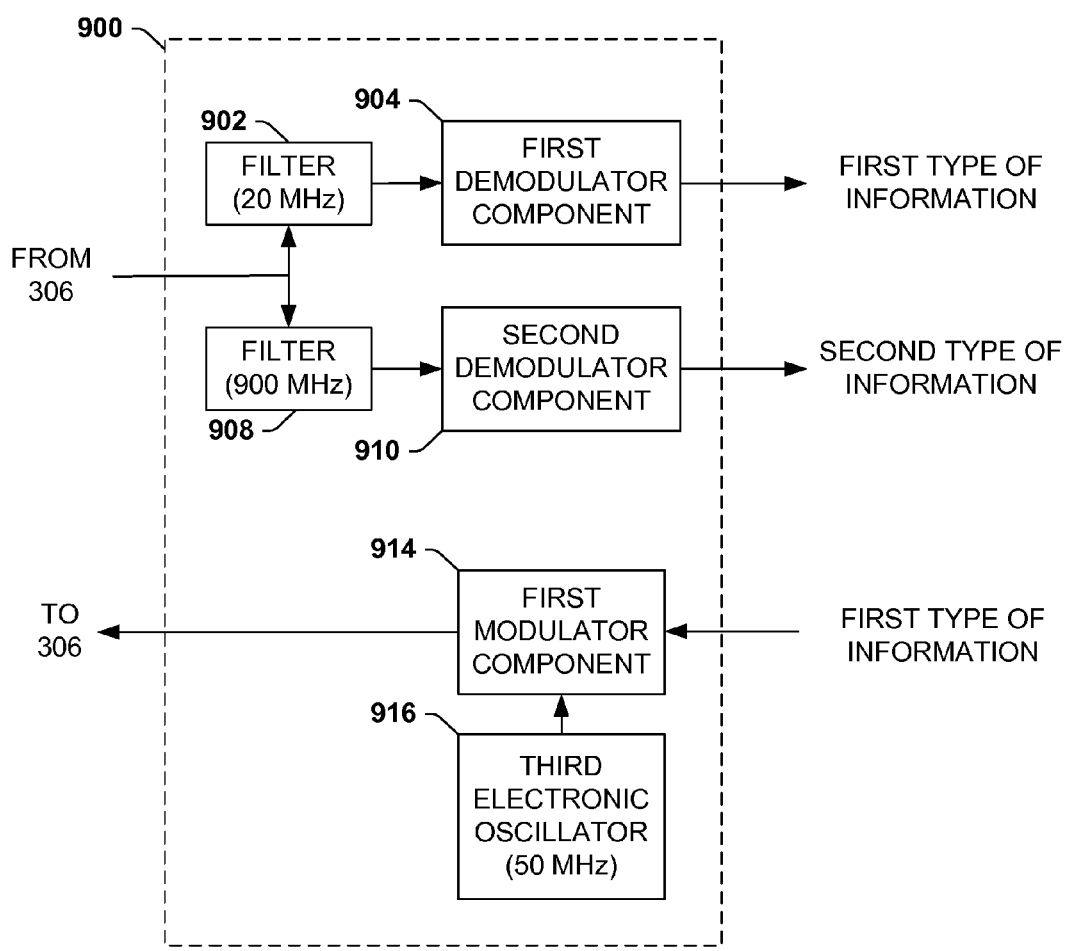
FIG. 9 illustrates a component block diagram of an example transceiver.

FIG. 9 illustrates yet another embodiment of an example transceiver 900 configured to illustrate how a transceiver may be configured for bi-directional communication using one or more multiplexing techniques to create logical channels. More specifically, FIG. 9 illustrates an example arrangement of a transceiver 900 configured to create three logical channels using a frequency-division multiplexing technique. In the illustrated embodiment, two of the logical channels are being utilized to receive information conveyed across a contactless data-link and one of the logical channels is being utilized to transmit information across the contactless data-link, although other arrangements and/or uses for the logical channels are contemplated.

In the illustrated embodiment, the three logical channels are created using three carrier signals, respectively having a different frequency. For example, a first receiver (e.g., comprised of a first filter 902, and a first demodulator component 904) is configured to receive signals having a frequency within a specified frequency range of about 10 MHz to about 30 MHz, for example, and a second receiver (e.g., comprised of a second filter 908 and a second demodulator component 910) is configured to receive signals having a frequency within a specified frequency range of about 850 MHz to about 950 MHz, for example. A first transmitter of the transceiver (e.g., comprised of a first modulator component 914 and a third electronic oscillator 916) may be configured to transmit signals across the contactless data-link having a frequency of about 35-65 MHz, for example. It may be appreciated that the components illustrated herein may perform functions similar to the functions described with respect to FIGS. 4 and 5, and thus a description of such functionality may not be repeated with respect to FIG. 9.

By dividing the frequency domain, a plurality of logical channels may be created through which various types of information may be (concurrently) conveyed across the contactless data-link mono-directionally or bi-directionally. For example, as illustrated, the example transceiver may be configured to convey a first type of information (e.g., control data) across the contactless data-link bi-directionally (e.g., using two logical channels, one for sending and one for receiving) and may be configured to merely receive (e.g., and not transmit) (e.g., using merely one logical channel for receiving) a second type of information from the contactless data-link.

It may be appreciated that although the example transceiver 900 illustrates example components for creating a bi-direction communication system using frequency-division multiplexing, other types of multiplexing, such as code-division and/or time division multiplexing, for example, may be utilized to create a bi-direction communication system for communicating information across a contactless data-link.

Figure 10:
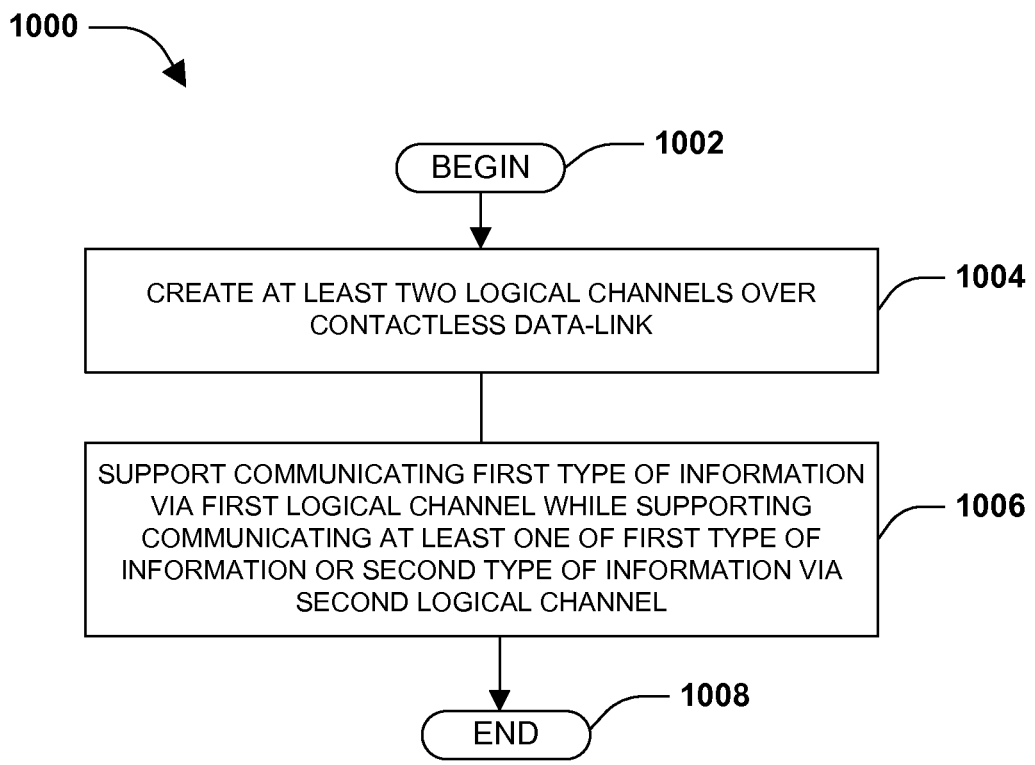
FIG. 10 illustrates an example flow diagram providing an example method for communicating information between a rotating member and a stationary member of a computed tomography (CT) system.

FIG. 10 illustrates an example method 1000 for communicating information between a rotating member and a stationary member of a computed tomography (CT) system. By way of example, the method 1000 may be utilized to communicate imaging data, control data (e.g., including status information of one or more components), and/or time data between the rotating member and the stationary member.

The example method begins at 1002 and at least two logical channels are created over a contactless data-link of the CT system at 1004. That is, stated differently, a contactless data-link may comprise one or more physical channels through which information is to be conveyed, and two or more sub-channels may be created via logic (e.g., dividing at least one physical channel into two or more logical channels). In this way, a number of channels through which information may be conveyed can be greater than a number of physical channels available on the contactless data-link. For example, in one embodiment, the contactless data-link comprises merely one physical channel, which may be logically divided into a plurality of logical channels to facilitate the transfer of information bi-directionally and/or to facilitate the transfer of multiple types of information (concurrently), for example, via the contactless data-link.

To logically create the two or more logical channels, frequency-division multiplexing, time-division multiplexing, code-division multiplexing, and/or other multiplexing techniques may be applied. The multiplexing technique utilized may depend upon, among other things, whether the contactless data-link is configured to support analog signals, digital signals, or both. Further, the multiplexing technique utilized may depend upon an available bandwidth of the data-link. For example, frequency-division multiplexing may be more desirable where there is a large amount of bandwidth, whereas time-division multiplexing may be more desirable where the available bandwidth is smaller.

Other techniques are also contemplated for creating the two or more logical channels. For example, two or more logical channels may be created via a circuit hybrid, such as described with respect to FIG. 8, configured to determine a direction of a signal and redirect the signal based upon the determined direction.

At 1008 in the example method 1000, communicating a first type of information is supported via a first logical channel of the two or more logical channels created at 1004 and communicating at least one of the first type of information or a second type of information is supported via a second logical channel of the two or more logical channels. That is, stated differently, the first logical channel is configured to communicate a first type of information (e.g., in a first direction) across the contactless data-link. The second logical channel is configured to communicate the first type of information (e.g., in a second direction different than (e.g., opposite to) the first direction), and/or to communicate a second type of information (e.g., in either the first direction or the second direction) across the contactless data-link.

In one embodiment, information may be communicated via the first and second channels concurrently. For example, the first type of information may be communicated bi-directionally and/or two or more types of information may be conveyed across the contactless data-link concurrently.

Further, in one or more embodiments, the first logical channel and/or the second logical channel may be initially configured to support an initial bit rate (e.g., or bandwidth), which may be periodically adjusted to accommodate changes in an amount of information required to be transmitted over the contactless data-link using the logical channel. By way of example, the first logical channel may be initially configured to support a first bit rate (e.g., 50 megabits per second). During an examination of an object via the CT system, the supported bit rate of the first logical channel may be adjusted from the first bit rate to a second bit rate (e.g., 100 megabits per second) to accommodate transferring information across the first logical channel more quickly (e.g., because an amount of information of a type the first logical channel is configured to support has increased). In this way, a bit rate and/or bandwidth of one or more logical channels may be dynamically adjusted to accommodate changes in the amount and/or type(s) of information a transceiver configured to transmit the information across the contactless data-link is receiving.

Figure 11:
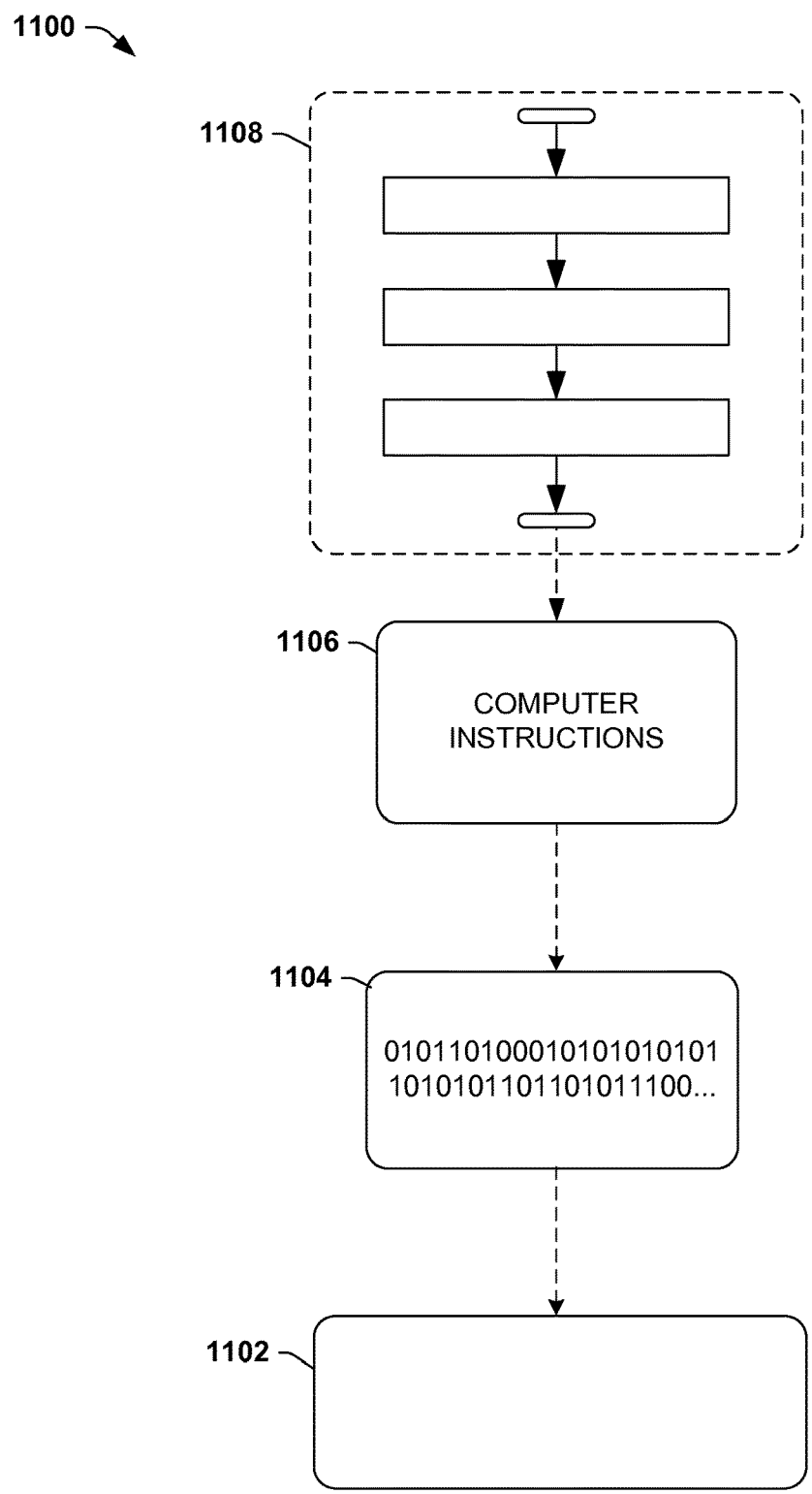
FIG. 11 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein (e.g., via a processing unit and/or memory). An example computer-readable medium that may be devised in these ways is illustrated in FIG. 11, wherein the implementation 1100 comprises a computer-readable medium 1102 (e.g., a CD-R, DVD-R, or a platter of a hard disk drive), on which is encoded computer-readable data 1104. This computer-readable data 1104 in turn comprises a set of processor-executable instructions 1106 configured to operate according to one or more of the principles set forth herein. In one such embodiment 1100, the processor-executable instructions 1106 may be configured to perform a method 1108, such as at least some of the example method 1000 of FIG. 10, for example. In another such embodiment, the processor-executable instructions 1106 may be configured to implement a system, such as at least some of the exemplary environment 100 of FIG. 1, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A communication system for communicating information between a rotating member and a stationary member of a computed tomography (CT) system, comprising:
    a contactless data-link comprising a rotating portion operably coupled to the rotating member of the CT system and a stationary portion operably coupled to the stationary member of the CT system, wherein:
        the rotating portion is separated from the stationary portion via an airgap, and
        the contactless data-link comprises a first physical channel consisting of a first winding on the rotating portion and a second winding on the stationary portion; and
    a transceiver configured to create at least two logical channels over the contactless data-link on the first physical channel.

2. The system of claim 1, wherein:
    a first logical channel of the at least two logical channels is configured for communication in a first direction, and
    a second logical channel of the at least two logical channels is configured for communication in a second direction different than the first direction.

3. The system of claim 1, wherein:
    a first logical channel of the at least two logical channels is configured to communicate a first type of information, and
    a second logical channel of the at least two logical channels is configured to communicate a second type of information different than the first type of information.

4. The system of claim 3, wherein the first type of information corresponds to imaging data and the second type of information corresponds to at least one of control data or timing data.

5. The system of claim 1, wherein:
    a first logical channel of the at least two logical channels is configured to transmit data at a first bit rate, and
    a second logical channel of the at least two logical channels is configured to transmit data at a second bit rate different than the first bit rate.

6. The system of claim 1, wherein the transceiver comprises at least one of a multiplexer or a demultiplexer.

7. The system of claim 1, wherein the transceiver is configured to create the at least two logical channels via frequency-division multiplexing.

8. The system of claim 1, wherein the transceiver comprises one or more frequency filters configured to filter signals received via the contactless data-link based upon a frequency.

9. The system of claim 1, wherein the transceiver is configured to create the at least two logical channels via time-division multiplexing.

10. The system of claim 1, wherein the transceiver configured to create the at least two logical channels via code-division multiplexing.

11. The system of claim 1, wherein the contactless data-link comprises at least one of a capacitive link or an optical link.

12. A method for communicating information between a rotating member and a stationary member of a computed tomography (CT) system, comprising:
creating at least two logical channels on a first physical channel of a contactless data-link that communicatively couples the rotating member and the stationary member, wherein:
the first physical channel consists of a first winding on the rotating member and a second winding on the stationary member,
a first logical channel of the at least two logical channels is configured to communicate a first type of information in a first direction, and
a second logical channel of the at least two logical channels is configured to at least one of:
communicate the first type of information in a second direction;
communicate a second type of information in the second direction; or
communicate the second type of information in the first direction.

13. The method of claim 12, wherein the creating at least two logical channels over a contactless data-link comprises:
creating the at least two logical channels using frequency-division multiplexing.

14. The method of claim 12, comprising:
supporting communicating the first type of information via the first logical channel while concurrently supporting communicating at least one of the first type of information or the second type of information via the second logical channel.

15. The method of claim 12, wherein:
the first logical channel supports a first bit rate prior to an examination of an object via the CT system, and
the method comprises:
performing the examination of the object via the CT system; and
adjusting a bit rate of the first logical channel from the first bit rate to a second bit rate during the examination of the object.

16. The method of claim 12, wherein the creating at least two logical channels over a contactless data-link comprises creating the at least two logical channels using time-division multiplexing.

17. The method of claim 12, wherein the creating at least two logical channels over a contactless data-link comprises creating the at least two logical channels using code-divisional multiplexing.

18. A computed tomography (CT) system, comprising:
a radiation source;
a detector array;
a rotating member configured to rotate the radiation source and the detector array about an object under examination;
a contactless data-link comprising a rotating portion operably coupled to the rotating member and a stationary portion operably coupled to a stationary member of the CT system, wherein:
the rotating portion is separated from the stationary portion via an airgap, and
the contactless data-link comprises a first physical channel consisting of a first winding on the rotating portion and a second winding on the stationary portion; and
a transceiver configured to provide for two-way communication on the first physical channel.

19. The system of claim 18, the transceiver configured to create at least two logical channels from the first physical channel, wherein the at least two logical channels are created using at least one of:
frequency-division multiplexing;
time-division multiplexing; or
code-division multiplexing.

20. The system of claim 18, wherein the transceiver comprises a circuit hybrid configured to direct signals received from the contactless data-link to a receiver portion of the transceiver and to direct signals transmitted from a transmitter portion of the transceiver to the contactless data-link.

* * * * *